US00PP19989P2

(12) United States Plant Patent
Klemm

(10) Patent No.: US PP19,989 P2
(45) Date of Patent: May 12, 2009

(54) **NEW GUINEA *IMPATIENS* PLANT NAMED 'KLENI07088'**

(50) Latin Name: *Impatiens hawkeri*
Varietal Denomination: KLENI07088

(75) Inventor: Nils Klemm, Stuttgart (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/075,744

(22) Filed: Mar. 13, 2008

(51) Int. Cl.
*A01H 5/00* (2006.01)

(52) U.S. Cl. ..... Plt./318.4

(58) Field of Classification Search ..... Plt./318.4
See application file for complete search history.

*Primary Examiner*—S. B. McCormick Ewoldt
(74) *Attorney, Agent, or Firm*—Jondle & Associates, P.C.

(57) ABSTRACT

A New Guinea *Impatiens* plant particularly distinguished by large round to oval flowers with a brilliant pink-blue color, medium precocity, compact, round plant habit and continuous flowering year around, is described.

1 Drawing Sheet

Genus and species: *Impatiens hawkeri* W. Bull.
Variety denomination:
'KLENI07088'.

BACKGROUND OF THE NEW PLANT

The present invention comprises a new and distinct cultivar of New Guinea *Impatiens,* botanically known as *Impatiens hawkeri* W. Bull, and hereinafter referred to by the cultivar name 'KLENI07088'. The new cultivar originated from a hybridization made in autumn of the year 2003 in Stuttgart, Germany. The female parent was the *Impatiens* plant 'KLEI04074' (U.S. Pat. No. 17,981), while the male parent was the proprietary *Impatiens* plant 'A 205' (unpatented).

The new cultivar was first propagated in 2004 in Stuttgart, Germany and has been asexually reproduced repeatedly by vegetative cuttings in Stuttgart, Germany over seven generations. The present invention has been found to retain its distinctive characteristics through successive asexual propagations.

Plant Breeder's Rights for this cultivar were applied for in Switzerland, on Mar. 30, 2007. 'KLENI07088' has not been made publicly available more than one year prior to filing of this application.

SUMMARY OF THE INVENTION

The following are the most outstanding and distinguishing characteristics of this new cultivar when grown under normal horticultural practices in a greenhouse in Stuttgart, Germany.

1. Brilliant pink-blue color;
2. Large round, oval flowers;
3. Medium precocity;
4. Compact and round plant habit; and
5. Continuous flowering year-around

DESCRIPTION OF PHOTOGRAPH

This New Guinea *Impatiens* plant is illustrated by the accompanying photograph which shows overall plant habit including blooms, buds, and foliage of the plant; the colors shown are as true as can be reasonably obtained by conventional photographic procedures. The photograph is of a plant about four and a half months old, grown in a greenhouse in Stuttgart, Germany, in the January 2008.

DESCRIPTION OF THE NEW CULTIVAR

The following detailed descriptions set forth the distinctive characteristics of 'KLENI07088'. The data which defines these characteristics were collected from asexual reproductions carried out in Stuttgart, Germany. The plant history was taken on four and a half month old plants which were planted as rooted cuttings in 10 cm pots in January 2008, and then grown in a greenhouse with covered glass. Color readings were taken under artificial light of 20,000 lux in the greenhouse. Color references are primarily to the R.H.S. Colour Chart of The Royal Horticultural Society of London (R.H.S.) (2001).

DETAILED BOTANICAL DESCRIPTION OF THE NEW PLANT

Classification:
- *Family.*—Balsaminaceae.
- *Botanical.*—*Impatiens hawkeri.*
- *Common name.*—New Guinea *Impatiens.*

Growth:
- *Growth and branching habit.*—Compact; round.
- *Height.*—16 cm.
- *Width.*—30 cm.
- *Propagation.*—Cuttings.
- *Time to produce a finished flowering plant.*—First blooms after 42 days in spring.
- *Time to initiate and develop roots.*—About 21 days.

Branches:
- *Average number.*—10.
- *Length of branches.*—11 cm.
- *Internode length.*—4 cm.
- *Diameter of branches.*—0.7 cm.
- *Stem color.*—RHS 174A.

Leaves:

*Arrangement.*—Base of the plant: Opposite. Middle and upper section of the plant: Whorled.

*Size.*—Length: 11 cm. Width: 4.5 cm.

*Shape.*—Oblong to lanceolate.

*Apex.*—Acuminate.

*Base.*—Acuminate.

*Margin.*—Shallowly serrated.

*Color* (*mature leaves*).—Upper surface: RHS 139A. Lower surface: RHS 138A.

*Color* (*immature leaves*).—Upper surface: RHS 139B. Lower surface: RHS 139C.

*Texture* (*both surfaces*).—Leathery, glossy.

*Venation color.*—Upper surface: RHS 139D. Lower surface: RHS 63A.

*Variegation.*—Absent.

*Petioles.*—Length: 1.5 cm. Diameter: 0.4 cm. Color (both surfaces): RHS 63A to RHS 63C. Texture (both surfaces): Smooth.

Flower buds:

*Shape.*—Ovoid; completely closed: drop shaped.

*Size.*—Length: 2 cm; completely closed: 1 cm. Diameter: 1.5 cm; completely closed: 0.9 cm.

*Color.*—RHS 52A; completely closed: RHS 142B.

Inflorescence:

*Blooming habit.*—Continuous.

*Inflorescence type.*—Single; flowers arranged in clusters arising from leaf axles, flowers positioned above the foliage and face upward and outside.

*Number of flowers per node.*—1 to 2 plus 3 to 4 buds.

*Flowering season.*—April to fall.

*Lastingness of individual blooms on the plant.*—14 to 21 days.

*Peduncle.*—Color: RHS 139B. Size: Length: 4.5 cm. Diameter: 0.2 cm. Texture: Smooth.

Flowers:

*Number of petals.*—5.

*Shape of corolla.*—Round oval.

*Corolla size.*—Length: About 7 cm. Width: About 7 cm. Depth: 1 cm.

Petals:

*Shape.*—Cordate.

*Apex.*—Petals are medium incised in the middle.

*Base.*—Round to acute.

*Margin.*—Entire.

*Size.*—Top petals: Length: About 3 cm. Width: About 3 cm. Lateral petals: Length: About 3 cm. Width: About 3 cm. Lower petals: Length: About 3 cm. Width: About 3 cm.

*Color* (*both surfaces*).—RHS 55A.

*Texture* (*both surfaces*).—Satiny, smooth.

Spur:

*Shape.*—Oblong to acute.

*Color.*—RHS 55A.

*Size.*—Length: 4.5 cm. Diameter: Base: 0.4 cm. Apex: 0.1 cm.

Reproductive organs:

*Stamens.*—Number: 5 stamens are fused and form a cap over the ovary. Stamen color (upper surface color): RHS 55A; with RHS 11C on the tip. Pollen color: Cream.

*Pistils.*—Style and stigma: Like hairs arranged in a circle. Ovary: Shape: Ovate. Length: 0.4 cm. Color: RHS 144C.

Fruit and seed set: No seed set observed.

Disease and insect resistance: No particular resistance or susceptibility has been observed.

COMPARISON WITH PARENTAL AND COMMERCIAL CULTIVARS

'KLENI07088' differs from the female parent 'KLEI04074' (U.S. Pat. No. 17,981) by having large, pink-blue flowers and a compact, round habit, while 'KLEI04074' has medium, pink-salmon flowers with a freely branching habit.

'KLENI07088' differs from the male parent 'A 205' (unpatented), by having pink-blue flowers, and foliage that is a lighter green color, while 'A 205' has pink-red flowers and foliage that is a medium-green color.

'KLENI07088' differs from the commercial cultivar 'Vienna' (U.S. Pat. No. 11,706) by having pink-blue flowers, while 'Vienna' has apple-blossom colored flowers. Additionally, 'KLENI07088' has a compact, round habit with foliage that is a lighter green color, while 'Vienna' has a freely branching habit and foliage with a medium-green color.

I claim:

1. A new and distinct cultivar of New Guinea *Impatiens* plant as shown and described herein.

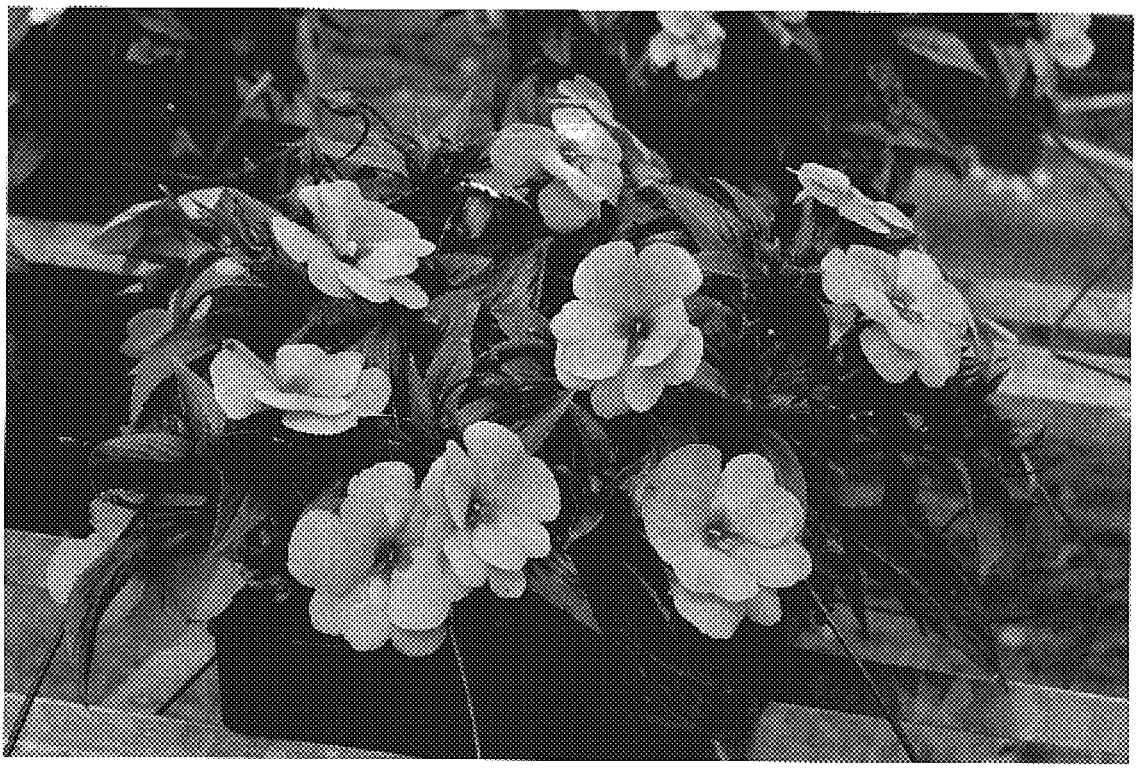

* * * * *